(12) United States Patent
Amiral

(10) Patent No.: US 9,518,286 B2
(45) Date of Patent: Dec. 13, 2016

(54) METHOD FOR ASSAYING PLASMINOGEN IN A LIQUID MEDIUM, ASSOCIATED COMPOSITIONS AND KIT

(71) Applicant: SYSMEX CORPORATION, Kobe-shi, Hyogo (JP)

(72) Inventor: Jean Amiral, Francoville (FR)

(73) Assignee: SYSMEX CORPORATION, Hyogo (JP)

(*) Notice: Subject to any disclaimer, the term of this patent is extended or adjusted under 35 U.S.C. 154(b) by 0 days.

(21) Appl. No.: 14/198,072

(22) Filed: Mar. 5, 2014

(65) Prior Publication Data
US 2014/0186865 A1  Jul. 3, 2014

Related U.S. Application Data

(63) Continuation of application No. PCT/IB2012/054634, filed on Sep. 7, 2012.

(30) Foreign Application Priority Data

Sep. 7, 2011 (FR) ........................... 11 57948

(51) Int. Cl.
*C12Q 1/56* (2006.01)
*G01N 33/86* (2006.01)

(52) U.S. Cl.
CPC .............. *C12Q 1/56* (2013.01); *G01N 33/86* (2013.01)

(58) Field of Classification Search
None
See application file for complete search history.

(56) References Cited

U.S. PATENT DOCUMENTS

| | | | | |
|---|---|---|---|---|
| 5,288,490 A * | 2/1994 | Budzynski | ............. | A61K 38/49 424/94.3 |
| 5,879,923 A | 3/1999 | Yago et al. | | |
| 6,020,181 A * | 2/2000 | Bini | ............................ | 435/226 |
| 2009/0011520 A1* | 1/2009 | Pilgrim | .................. | G01N 33/86 436/501 |
| 2010/0028372 A1* | 2/2010 | Jezek | ...................... | A61K 38/27 424/184.1 |

FOREIGN PATENT DOCUMENTS

| | | |
|---|---|---|
| JP | 63105698 A | 5/1988 |
| JP | 4505326 A | 9/1992 |
| WO | 9014102 | 11/1990 |
| WO | 2013035074 A9 | 3/2013 |

OTHER PUBLICATIONS

Cuoto et al., "Analysis of five streptokinase formulations using the euglobulin lysis test and the plasminogen activation assay", Brazilian Journal of Medical and Biological Research 2004, vol. 37, pp. 1889-1894.*
Ammollo et al., "Dabigatran enhances clot susceptibility to fibrinolysis by mechanisms dependent on and independent of thrombinactivatable fibrinolysis inhibitor", Journal of Thrombosis and Haemostasis 2010, vol. 8, pp. 790-798.*
Takeda et al., "The activation of GLU-and LYS-plasminogens by streptokinase: Effects of fibrin, fibrinogen and their degradation products", Thrombosis Research, 37(3):465-475 (1985).
Nieuwenhuizen, "Fibrin-Mediated Plasminogen Activation", Annals of the NY Academy of Sciences, 936, (1):237-246 (2001).
Nieuwenhuizen, "Sites in fibrin involved in the acceleration of plasminogen activation by t-PA. Possible role of fibrin polymerisation", Thrombosis Research, 75(3):343-347 (1994).
Strickland et al., "Enhancement of the Strepto Kinase Catalyzed Activation of human plasminogen by human fibrinogen and its plasminolysis products", Biochemistry, 21(4):721-728 (1982).
Chibber et al., "Fibrinogen and its cleavage products on activation of human plasminogen by streptokinase", Biochemistry, 24(14):3429-3434 (1985).
International Search Report for PCT/IB2012/054634 dated Nov. 21, 2012.
Reed et al., "A catalytic switch and the conversion of streptokinase to a fibrin-targeted plasminogen activator", Proc. Natl. Acad. Sci., USA, 96(16):8879-8883 (1999).
Testzym® S PLG, Chromogenix Instrumentation Laboratory SpA, 769303-007 (Apr. 2008), http://www.sekisuimedical-csc.com/product/blood/_icsFiles/afieldfile/2014/04/17/9C.pdf.
HDL-C Reagent KL "Kokusai", HDL-cholesterol Kit, Sysmex (Nov. 2009), http://www.info.pmda.go.jp/downfiles/ivd/PDF/480585_28A2X00030000033_A_01_01.pdf.

* cited by examiner

*Primary Examiner* — Renee Claytor
*Assistant Examiner* — Michelle F Paguio Frising
(74) *Attorney, Agent, or Firm* — Sughrue Mion, PLLC

(57) ABSTRACT

The invention relates to a method for assaying plasminogen in a sample comprising a step consisting in particular of reacting a streptokinase (R1), and a streptokinase activator, with a control solution or a diluted plasma sample, in which the streptokinase activator is selected from the group comprising a fibrin DD fragment and/or at least one DD fragment derivative.

The invention also relates to a liquid composition, a plasminogen assay kit for implementing this method and the use of a streptokinase activator selected from the group comprising a fibrin DD fragment and/or at least one DD fragment derivative.

12 Claims, 5 Drawing Sheets

A

B

METHOD FOR ASSAYING PLASMINOGEN IN A LIQUID MEDIUM, ASSOCIATED COMPOSITIONS AND KIT

TECHNICAL FIELD OF THE INVENTION

The invention relates to the field of methods for assaying plasminogen in a sample, in particular by means of liquid reagents, in particular by means of ready-to-use reagents that can be stored for a long period of time.

This type of assay requires an activation of the plasminogen of the sample, which is generally done with streptokinase.

In this context, a solution consists of using a streptokinase with a streptokinase activator, which is fibrinogen. However, the fibrinogen is difficult to preserve in liquid form, resulting in assay results that can be modified as a function of fibrinogen preservation time.

PRIOR ART

Thus, to overcome these disadvantages, U.S. Pat. No. 5,879,923 discloses a plasmin solution stabilized by oligopeptides, determined amino acids. This solution is not entirely satisfactory because it is limited to the stabilization of the plasmin solution and is not suitable for stabilizing the plasminogen activator solution such as fibrinogen. In addition, this solution is not satisfactory for an assay of the plasminogen present in the blood of a patient based on ready-to-use liquid reagents prepared a long time before the patient's blood is taken.

DESCRIPTION OF THE INVENTION

The invention is intended to overcome the disadvantages of the prior art and in particular to propose a method for assaying plasminogen in a sample comprising steps comprising the steps of:
a—reacting
  i—a streptokinase, and a streptokinase activator,
  ii—with a control solution or a diluted plasma sample,
b—tracking said reaction using means for tracking the reaction (SPm),
c—determining the amount of plasminogen in the control solution or in the diluted plasma sample, as a function of the result of the tracking of said reaction. In particular embodiments, the methods consist of the steps described above According to the invention, the streptokinase activator used in the methods provided herein is one or more compounds selected from the group consisting of a fibrin DD fragment and/or a DD fragment derivative. By DD (or D-dimer) fragment, we mean a sub-fragment of fibrin containing two cross-linked D domains each from a different fibrogen molecule and that can be obtained, for example, by enzymatic lysis of fibrin.

Thus, the DD fragment used in this invention may come from a fibrin or lysed blood clot. It is also possible to use a recombinant DD fragment. A non-purified DD fragment may also be used, for example a fibrin degradation fraction. By DD fragment derivative, we mean a molecule comprising at least some of the DD fragment as defined above, in particular the amino acids of the DD fragment involved in the streptokinase activation. In particular embodiments, the derivative has at least 70% sequence identity to the DD fragment, more particularly at least 80%, most particularly at least 90% or more than 95% sequence identity with the DD fragment.

In further particular embodiments, the DD fragment derivative may comprise, for example, more amino acids than the DD fragment, and include for instance the D-dimer/fragment E complex.

The means or compound for tracking the reaction (SPm) may, for example, be a molecule grafted on a substrate, on an enzyme product formed by streptokinase and the streptokinase activator, or on said enzyme. Such a graft is performed, for example, by chemical synthesis. The means for tracking the reaction (SPm) may also be a molecule capable of being associated with a substrate, with a product of said enzyme or with said enzyme.

The means or compounds for tracking are chosen so as to be capable of tracking the reaction of said enzyme, for example, by generating or causing the disappearance of a colour or fluorescence or by modifying the absorbance of the reaction medium.

In particular embodiments, the compound for tracking the reaction is a chromogenic substrate specific for plasmin and plasmin-streptokinase complexes. Examples of such compounds are known in the art, such as but not limited to S-2403™, S-2251™ sold by Chromogenix and SPm41 sold by the company Hyphen Biomed.

In particular embodiments, the reaction can be performed in the presence of an anticoagulant, preferably hirudin or any other thrombin inhibitor.

Advantageously, the method comprises, prior to reaction step a), a step of storing the streptokinase activator in a ready-to-use solution. Thus, the method does not require preparation of a streptokinase activator solution immediately before use. In addition, the streptokinase activators are stable in solution and can be preserved, for example, with streptokinase, without altering its physicochemical properties and its efficacy in the performance of the plasminogen assay. In particular embodiments, the streptokinease and streptokinase activator can be packaged together.

In particular embodiments, the streptokinase activator storage step is performed at a temperature of between −20° C. and 37° C. In particular embodiments, the streptokinase activator is stored at between 2-10° C., more particularly between 4-8° C. In particular embodiments, the streptokinase activator is suitable for storage at room temperature or does not require specific storage conditions.

According to an advantageous embodiment, the storage step is performed for a period greater than 12 hours, preferably between 24 hours and 24 months, in particular between 24 hours and 18 months.

Optionally, the streptokinase activator is stored in the presence of preservatives and/or antibiotics such as ciprofloxacin.

Advantageously, the method also comprises a step of pre-incubation of the streptokinase (R1), and of the streptokinase activator, at around 37° C., which step is performed before said reaction step a).

According to a particular embodiment, the reaction step a) is performed at around 37° C., preferably for around 3 to 6 minutes.

According to a particular embodiment, the reaction step a) is stopped by an acidification step, preferably by adding citric acid.

A further objective of the invention concerns a composition for assaying plasminogen present in a sample, in which said composition comprises a streptokinase activator, characterized in that the streptokinase activator is one or more compounds selected from the group consisting of a fibrin DD fragment and/or at least one DD fragment derivative.

In particular embodiments, the composition described above also comprises an anticoagulant, preferably hirudin.

In particular embodiments, the composition described above is in a ready-to-use solution.

In particular embodiments, the composition comprising the streptokinase activator comprises streptokinase.

In particular embodiments, the composition is particularly suitable as a ready-to-use solution. In particular embodiments, the composition comprises a solution of streptokinase activator at around 100 µg/ml or which can be easily diluted to a concentration of 100 µg/ml, such as a concentration between 100 µg/ml and 1 mg/ml. In particular embodiments the composition requires no further manipulations, including no further dilutions, prior to use.

In particular embodiments, the composition does not comprise fibrinogen. In more particular embodiments, the compositions comprise a DD fragment and/or one or more DD fragment derivatives, and does not comprise another streptokinase activator. In further particular embodiments, the compositions comprise only one streptokinase activator, more particularly a DD fragment and/or one or more DD fragment derivatives.

The invention also relates to a kit for assaying plasminogen in a sample comprising a composition described according to one or more of the embodiments above.

Advantageously, the kit for assaying described above is configured for implementing the method described above.

In particular, the invention relates to a kit for assaying plasminogen in a sample comprising one or more of a streptokinase, a streptokinase activator, and a means for tracking (SPm) a reaction between streptokinase, the streptokinase activator and a diluted plasma sample, in which the streptokinase activator is one or more compounds selected from the group consisting of a fibrin DD fragment and/or at least one DD fragment derivative. More particularly, specific kits are envisaged for in vitro use. This implies that the reagents are suitable for in vitro use and may comprise reagents, such as preservatives which are not compatible for in vivo use. In particular embodiments, the kit for assaying plasminogen in a sample comprises a streptokinase and a streptokinase activator selected from the group consisting of a fibrin DD fragment and/or at least one DD fragment derivative. In further particular embodiments, the kit further comprises a means for tracking (SPm) the reaction (i.e. the between streptokinase, the streptokinase activator and a diluted plasma sample).

In particular embodiments, the streptokinase and streptokinase activator are packaged together in the kit. In further particular embodiments, the streptokinase solution in the kit is particularly suited for use at about 12,500 to 15,000 IU/ml.

In particular embodiments, the kit for assaying is characterized by at least one composition calibrated by volume and quantity so as to be reacted with a control solution or a diluted plasma sample in order to quickly determine the amount of plasminogen in the control solution or the diluted plasma sample, on the basis of the tracking of the reaction between the enzyme and the substrate.

For example, the compositions of the kit are chosen so that a volume of streptokinase and streptokinase activator composition is mixed with a volume of a control solution or a diluted plasma sample. In particular embodiments, the compositions of the kit are chosen so that the streptokinase solution contains about 12,500 to 15,000 IU/ml. In particular embodiments, the streptokinase activator solution contains about 100 µg/ml.

A further objective of the invention consists of a use of a streptokinase activator for assaying plasminogen in a sample, with the streptokinase activator being selected from the group consisting of a fibrin DD fragment and/or at least one DD fragment derivative.

BRIEF DESCRIPTION OF THE FIGURES

Additional features, details and advantages will become clear from the following description, in reference to the appended figures, which show.

For greater clarity, identical or similar elements are denoted by the same reference signs in all of the figures.

DETAILED DESCRIPTION OF EMBODIMENTS OF THE INVENTION

Figure 1:
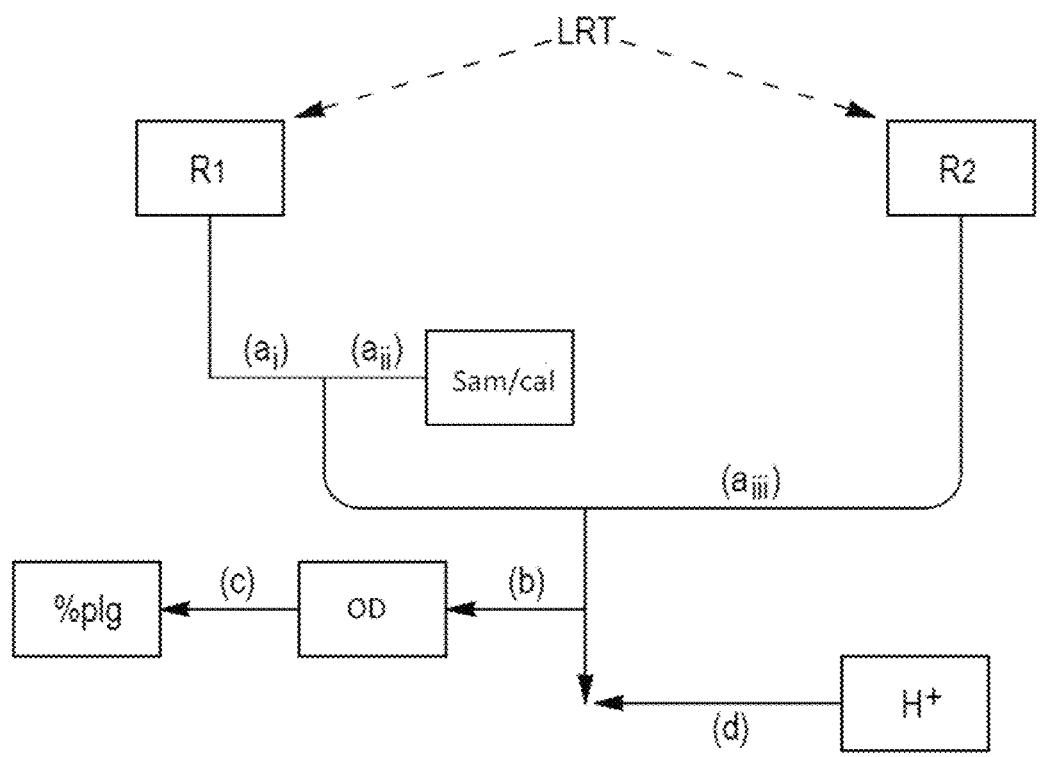
FIG. 1 provides a general diagram of the method according to particular embodiments of the invention.

In reference to FIG. 1, the embodiment of the method according to a preferred mode is based on compositions of reagents R1 and R2, which are, for example, stored in ready-to-use liquid form LRT.

The first reagent composition R1 comprises the DD fragment. DD is obtained by clotting fibrinogen to fibrin with thrombin in order to obtain a clot, which is then degraded by tPA in presence of plasminogen, to generate fibrin degradation products; DDimer is further purified using ion exchange chromatography and if required a complementary gel filtration chromatography. The DD fragment is provided in the first reagent composition R1 in a concentration preferably around 0.1 mg/ml; a base matrix comprising Tris, Na$_2$EDTA, NaCl and BSA is preferred, but other base matrices may be used. For a quality assay, preferably a so-called "Plg-free" DD fragment is used, i.e. comprising plasminogen in a trace state, or preferably no plasminogen.

The first reagent composition R1 also comprises at least one preservative, preferably ciprofloxacin, sodium azide at 0.9 g/l and hirudin at 0.25 ATU/ml.

Finally, the first reagent composition R1 comprises streptokinase. As indicated above, most particularly the streptokinase activatoris a fibrin D-dimer.

The second reagent composition R2 comprises a synthetic substrate SPm41 sold by the company Hyphen Biomed, which releases paranitroanilin in the presence of plasminogen (plg), streptokinase and fibrinogen (or DD fragment). R2 may also comprise another substrate of which the interaction with the enzyme (in this case, the plasminogen-streptokinase complex) modifies the absorbance or the fluorescence of the reaction medium.

Preferably, the second reagent composition R2 is buffered with an acid pH, preferably by means of tartaric acid.

In a step (ai-aii), a volume of the first reagent composition R1 is mixed with a volume of control solution (cal) or diluted plasma sample (Sam), and the mixture is incubated for 3 minutes, at 37° C.

In a step (aiii), a volume of the second reagent composition R2 is added to this mixture and it is mixed and incubated for 3 minutes at 37° C.

Then, in a step (b), the change in the reaction is observed by the modification in the absorbance or optical density (OD) correlated with the consumption of the substrate, in this case SPm41. In the case of SPm41, the absorbance is measured at 405 nm.

The variation in absorbance (OD) makes it possible to determine, in a step (c), the plasminogen content (% plg), for example by means of a calibration curve.

The reaction is preferably then stopped in a step (d), for example, by adding a volume of citric acid (H+) at 20 g/l.

Comparative plasminogen assay tests have been conducted with fibrinogen (+fbg) according to the prior art, without fibrinogen (−fbg), or with fibrinogen substitutes using fibrin derivatives, according to table 1 below:

TABLE 1 tests with fibrinogen substitutes:

| Manual method (WB) % Plg: | −fbg | +fbg at 0.7 mg/ml | with an FFE fragment at 0.05 mg/ml | with an FE fragment at 0.05 mg/ml | with an FD fragment at 0.10 mg/ml | with an DD fragment at 0.10 mg/ml |
|---|---|---|---|---|---|---|
| | | | OD (at 405 nm) | | | |
| C (1/20 = 150%) | 0.743 | 1.577 | 0.755 | 0.729 | 0.825 | 1.977 |
| C:2 | 0.298 | 0.742 | 0.291 | 0.271 | 0.304 | 0.991 |
| C:4 | 0.113 | 0.333 | 0.115 | 0.114 | 0.121 | 0.473 |
| C:8 | 0.047 | 0.152 | 0.049 | 0.047 | 0.053 | 0.210 |
| 0 | 0.003 | 0.010 | 0.001 | 0.005 | 0.005 | 0.006 |
| r2 (lin-lin) | 0.985 | 0.9976 | 0.9828 | 0.9792 | 0.9775 | 0.9995 |

In table 1, line C corresponds to a calibration composition with a dilution of 1/20 for a plasminogen concentration of 150%. Line C:2 corresponds to a calibration composition with a dilution of half that of line C, and so on and so forth until line C:8. Line 0 corresponds to a calibration composition with a plasminogen concentration of 0%. Line r2 corresponds to the square of the linear correlation coefficient of the calibration curves.

Figure 2:
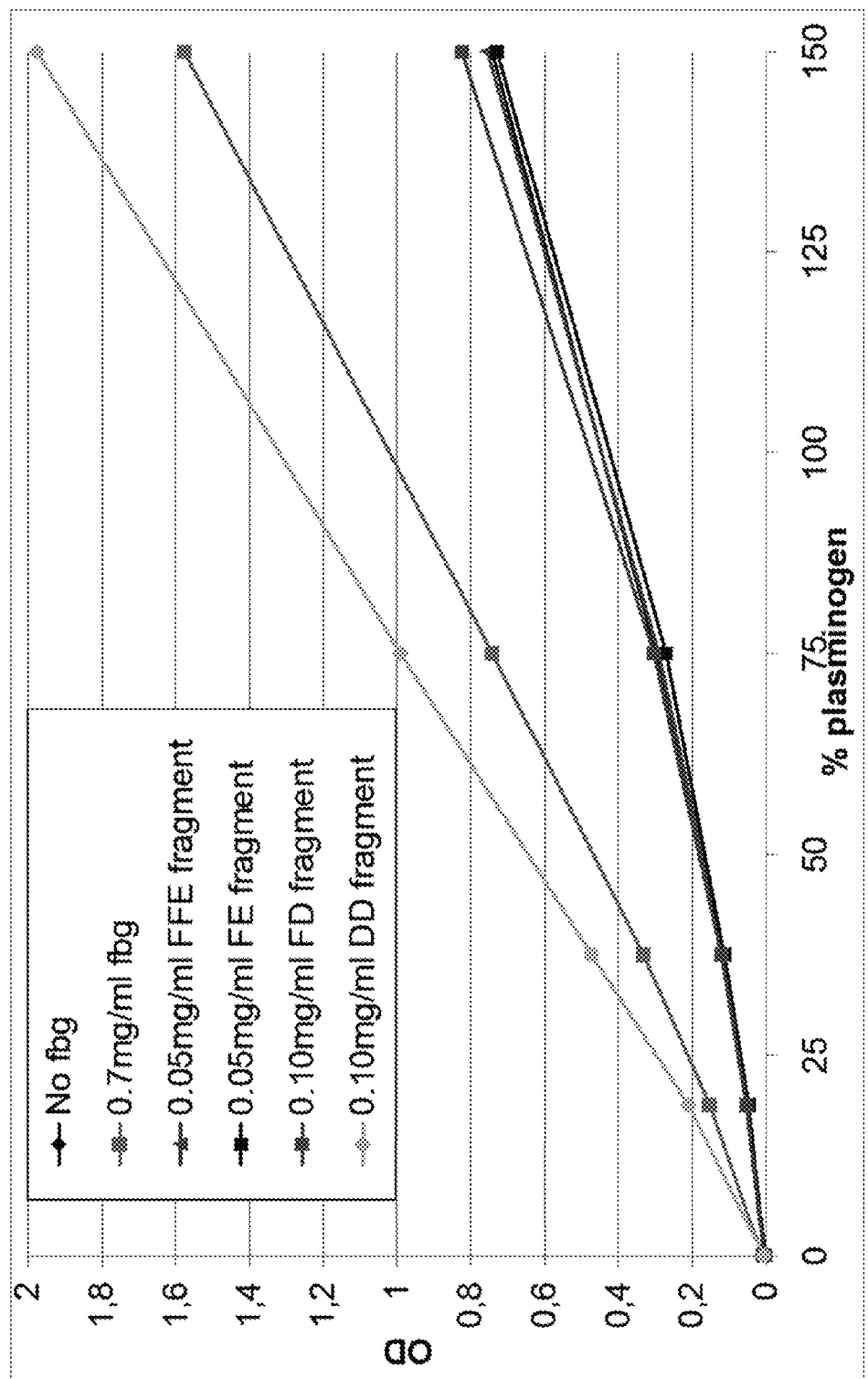
FIG. 2 provides a calibration curve in fibrinogen replacement tests.

The calibration curves of FIG. 2 correspond to the results of table 1 above. The y-coordinates correspond to the optical density values (OD) at 405 nm, and the x-coordinates correspond to the plasminogen content (% plg). These curves have references relating to the presence (+fbg) or the absence (−fbg) of fibrinogen, or to the different substitutes tested (FFE, FE, FD, DD) at the concentrations mentioned in table 1.

As can be seen in FIG. 2, the calibration curve corresponding to the test without fibrinogen (−fbg) substantially overlaps with those of the tests of fibrinogen replacement with fibrin FFE, FE, FD fragments.

Surprisingly, it is clear from FIG. 2 and table 1 that the curve (+DD) corresponding to the fibrin DD fragment appears to be of higher quality than the curve corresponding to the whole fibrinogen (+fbg). Indeed, the r2 coefficient is 0.9995 for DD by comparison with 0.9976 for the sample (+fbg), which means better linearity. In addition, the DD curve is above the +fbg curve, which means a higher OD and therefore a more exact quantification of the plasminogen content.

Tests for determining the optimal DD fragment content were also performed, according to table 2 below:

TABLE 2

Tests with different DD fragment contents:

| Manual method (WB) % Plg: | DD at 500 μg/ml | DD at 200 μg/ml | DD at 100 μg/ml | DD at 50 μg/ml | DD at 25 μg/ml |
|---|---|---|---|---|---|
| | | | OD (at 405 nm) | | |
| C (dilution 1/20 = 150%) | 2.246 | 2.125 | 2.003 | 1.723 | 1.433 |
| C:2 | 1.185 | 1.132 | 0.998 | 0.822 | 0.640 |
| C:4 | 0.592 | 0.560 | 0.467 | 0.368 | 0.257 |
| C:8 | 0.284 | 0.264 | 0.209 | 0.156 | 0.112 |
| 0 | 0.001 | 0.002 | 0.000 | 0.000 | 0.000 |

TABLE 2-continued

Tests with different DD fragment contents:

| Manual method (WB) % Plg: | DD at 500 μg/ml | DD at 200 μg/ml | DD at 100 μg/ml | DD at 50 μg/ml | DD at 25 μg/ml |
|---|---|---|---|---|---|
| | | | OD (at 405 nm) | | |
| r2 (lin-lin) | 0.9991 | 0.9987 | 0.9995 | 0.9983 | 0.9941 |

Figure 3:
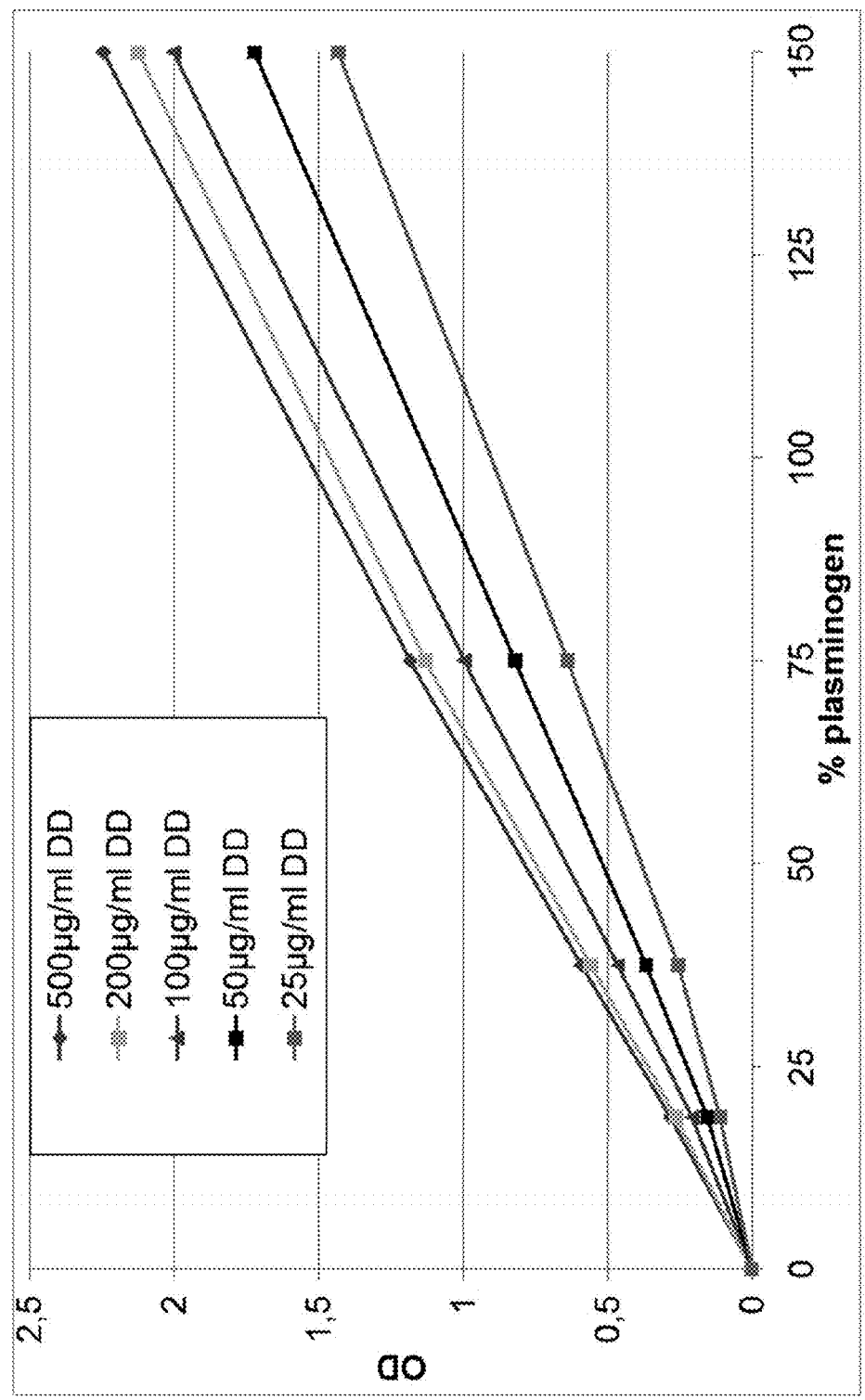
FIG. 3 provides a calibration curve in exemplary tests with different fibrin DD fragment concentrations.

The calibration curves of FIG. 3 correspond to the results of table 2 above. The y-coordinates correspond to the optical density values (OD) at 405 nm, and the x-coordinates correspond to the plasminogen content (% plg). The curves corresponding to table 2 thus have references relating to the concentration, in μg/ml, of the fibrin DD fragment in the different tests.

As can be seen in FIG. 3 and table 2, a DD fragment content of 100 μg/ml is enough to optimize the plasminogen assay. Indeed, with an r2 of 0.9995, the linearity is satisfactory and the curve is in an intermediate position with respect to those corresponding to the other DD fragment concentrations.

In addition, tests were conducted to determine the optimal streptokinase content in the following two R1 samples: one with fibrinogen at 0.7 mg/ml of which the results are shown in table 3; and the other with 100 μg/ml of DD fragment of which the results are shown in table 4.

TABLE 3 optimum streptokinase with 0.7 mg/ml of fibrinogen:
R1 with 0.7 mg/ml of fibrinogen/R2

| [streptokinase] | % plasminogen | | | | | r2 | ΔOD |
|---|---|---|---|---|---|---|---|
| IU/ml | 150 | 75 | 37.5 | 18.75 | 0 | (lin/lin) | (150-0%) |
| 0 | 0.044 | 0.024 | 0.015 | 0.010 | 0.002 | 0.9944 | 0.042 |
| 5000 | 1.357 | 0.597 | 0.273 | 0.125 | 0.023 | 0.9933 | 1.334 |
| 7500 | 1.581 | 0.720 | 0.333 | 0.157 | 0.017 | 0.9963 | 1.564 |
| 10000 | 1.697 | 0.788 | 0.360 | 0.175 | 0.012 | 0.9974 | 1.685 |
| 12500 | 1.771 | 0.843 | 0.400 | 0.195 | 0.016 | 0.9986 | 1.755 |
| 20000 | 1.860 | 0.926 | 0.455 | 0.208 | 0.012 | 0.9997 | 1.848 |
| 30000 | 1.877 | 0.94 | 0.470 | 0.234 | 0.015 | 0.9999 | 1.862 |

After analysis of the absorbance change curve as a function of the streptokinase concentration (not shown) corresponding to table 3, it is noted that, in the R1 sample with 0.7 mg/ml of fibrinogen, a plateau can be observed starting with a streptokinase concentration of around 20,000 IU/ml. In table 3, a ΔOD (150-0%) of 1.848 for line (2000 IU/ml) and 1.862 for line (30,000 IU/ml) is indeed observed. The optimal streptokinase concentration is thus estimated at 20,000 IU/ml, the value at which the OD no longer increases significantly.

TABLE 4

Optimum streptokinase with 100 μg/ml of DD fragment:
R1 with 100 μg/ml of DD fragment/R2

| [streptokinase] | % plasminogen | | | | | R2 | ΔOD |
|---|---|---|---|---|---|---|---|
| IU/ml | 150 | 75 | 37.5 | 18.75 | 0 | (lin/lin) | (150-0%) |
| 0 | 0.037 | 0.014 | 0.006 | 0.008 | 0 | 0.9552 | 0.037 |
| 5000 | 1.846 | 0.868 | 0.386 | 0.157 | 0 | 0.9977 | 1.846 |
| 7500 | 1.891 | 0.915 | 0.418 | 0.179 | 0 | 0.9991 | 1.891 |
| 10000 | 1.956 | 0.959 | 0.444 | 0.194 | 0.002 | 0.9992 | 1.954 |
| 12500 | 1.986 | 0.971 | 0.462 | 0.207 | 0 | 0.9995 | 1.986 |
| 20000 | 1.979 | 0.982 | 0.467 | 0.222 | 0 | 0.9998 | 1.979 |
| 30000 | 1.961 | 0.967 | 0.47 | 0.219 | 0 | 0.9998 | 1.961 |

Figure 4:
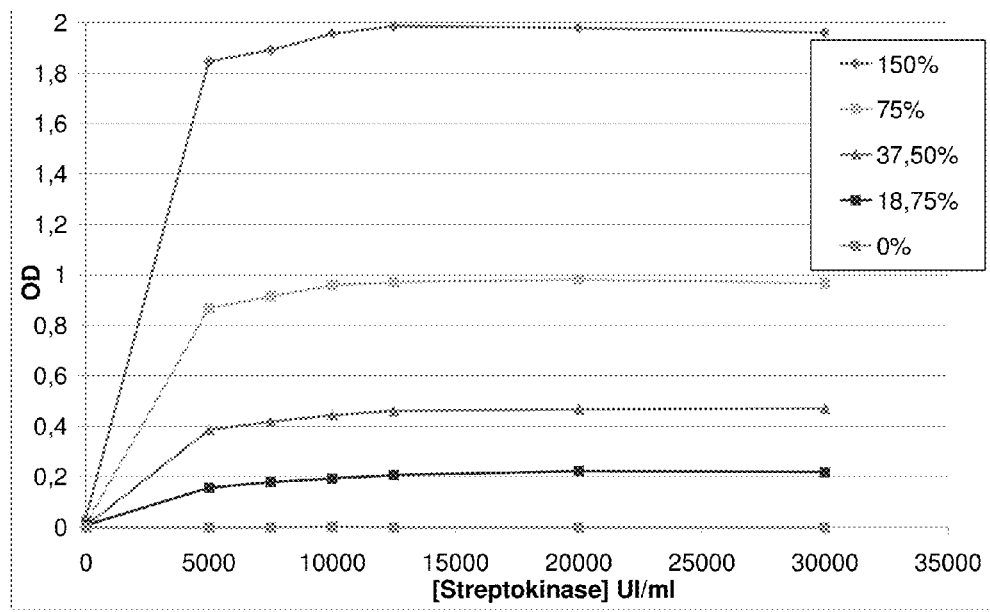
FIG. 4 provides curves for determining the optimal amount of streptokinase in exemplary embodiments.

As can be seen in the absorbance (DO) change curves as a function of the streptokinase concentration ([Strept] in IU/ml) shown in FIG. 4, and corresponding to table 4, a start of saturation of the curves can be observed starting with a streptokinase concentration of 5000 IU/ml. A plateau can be observed more clearly in FIG. 4 between 12,500/15,000 IU/ml. In parallel, in table 4, a ΔOD (150-0%) is noted of 1.954 and 1.986 for lines (12,500 and 15,000 IU/ml) and 1.961 for line (30,000 IU/ml). The optimal streptokinase concentration is thus estimated at between 12,500 and 15,000 IU/ml, preferably at 15,000 IU/ml.

Surprisingly, it is clear from table 4 and FIG. 4 that when the DD fragment is used, less streptokinase is needed (12,500 to 15,000 IU/ml for the +DD sample by comparison with 20,000 for the −fbg sample) and better results are obtained than with the whole fibrinogen. Indeed, the saturation of the OD begins at lower streptokinase concentrations (5000 IU/ml).

The stability of the R1 reagent composition comprising DD fragment was further investigated. To this end, an R1 reagent composition comprising the DD fragment at a concentration of 0.1 mg/mL, Streptokinase at 10000 UI/mL and an R2 reagent composition comprising the substrate SPm41 at a concentration of 2.25 mg/mL were used in the methods as described above. 200 μl of a sample with varying concentrations (obtained from a dilution of 1/30 corresponding to a concentration of 100%) was mixed with 200 μl of R1 reagent composition and incubated for 3 minutes at 37° C. Thereafter 200 μl of reagent composition R2 is added and the mixture is again incubated for 3 minutes at 37° C. The reaction is then stopped using 200 μl citric acid 2%.

The test was performed at different time points over 3 months time, whereby the reagents are kept at room temperature.

The results are illustrated in Table 5.

TABLE 5 reproducibility of assay over 3 month's time

| | % plasminogen | | | | | r2 | OD |
|---|---|---|---|---|---|---|---|
| Time | 150 1/20 | 75 1/40 | 37.5 1/80 | 18.75 1/160 | 0 0 | (lin/lin) | (150/0) |
| T0 | 2.500 | 1.251 | 0.579 | 0.261 | 0 | 0.9994 | 2.500 |
| T0 + 1 week | 2.858 | 1.537 | 0.711 | 0.346 | 0 | 0.9981 | 2.858 |
| T0 + 2 weeks | 2.776 | 1.430 | 0.638 | 0.257 | 0 | 0.9982 | 2.776 |
| T0 + 3 weeks | 2.329 | 1.302 | 0.625 | 0.299 | 0 | 0.9964 | 2.329 |
| T0 + 1 month | 2.698 | 1.384 | 0.620 | 0.229 | 0 | 0.9978 | 2.698 |
| T0 + 2 months | 2.693 | 1.314 | 0.628 | 0.238 | 0 | 0.9997 | 2.693 |
| T0 + 3 months | 2.532 | 1.276 | 0.626 | 0.25 | 0.007 | 0.9991 | 2.525 |

While the results obtained at 150% show some variability due to the involvement of different technicians at different time points, it is apparent from these data that the R1 reagent composition is stable at room temperature over prolonged periods of time and will result in comparable results when used over a 3 month time period.

Similarly, the stability of the R1 reagent composition was considered upon conservation at 30° C. in a water bath. The data are provided in Table 6 below. Other experimental conditions were as described above.

TABLE 6

Conservation at 30° C. of R1 reagent composition comprising DD-fragment

| | % plasminogen | | | | | r2 | ÄOD |
|---|---|---|---|---|---|---|---|
| Time | 150 1/20 | 75 1/40 | 37.5 1/80 | 18.75 1/160 | 0 0 | (lin/lin) | (150/0) |
| T0 (11/08/11) | 2.500 | 1.251 | 0.579 | 0.261 | 0 | 0.9994 | 2.500 |
| T0 + 1 weeks + 30° C. | 2.632 | 1.293 | 0.530 | 0.165 | 0 | 0.9957 | 2.632 |
| T0 + 2 weeks + 30° C. | 2.655 | 1.335 | 0.564 | 0.211 | 0 | 0.9973 | 2.655 |
| T0 + 3 weeks + 30° C. | 2.424 | 1.232 | 0.570 | 0.264 | 0 | 0.9992 | 2.424 |
| T0 + 4 weeks + 30° C. | 2.554 | 1.196 | 0.497 | 0.191 | 0 | 0.9963 | 2.554 |

Figure 5:
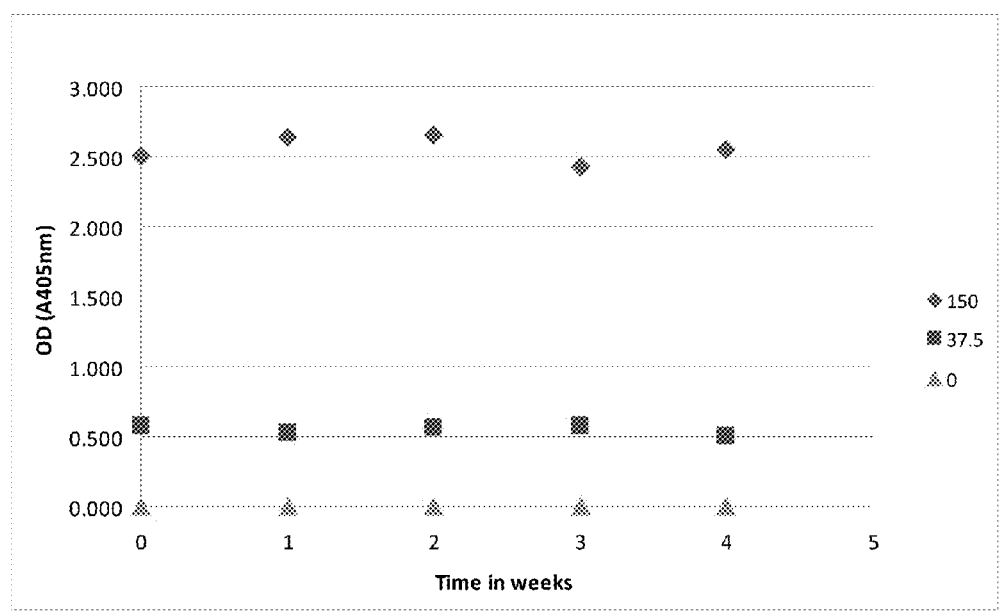
FIG. 5 illustrates the stability of an exemplary R1 reagent comprising the DD fragment (A) or, as a comparison, fibrinogen (B), upon incubation in a water bath at 30° C.
Figure 5:
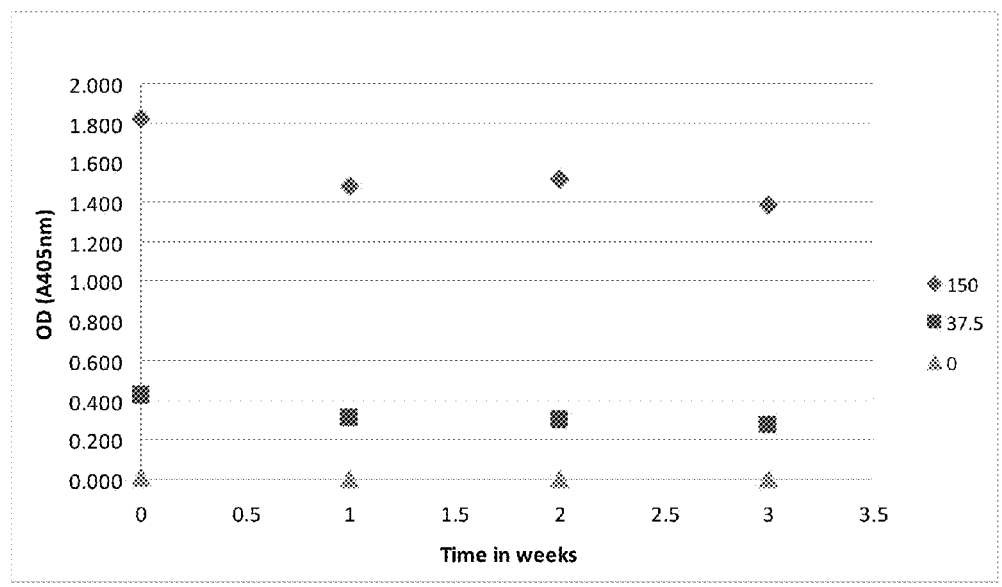

These data are illustrated in FIG. 5A.

A similar experiment was performed using an R1 reagent composition comprising fibrinogen at 0.7 mg/mL, and streptokinase at 11000 UI/mL. R2 reagent composition and experimental conditions were as described above. Incubation of R1 was at 30° C. in a waterbath. The data are provided in Table 7 below and FIG. 5B.

TABLE 7

Conservation at 30° C. of R1 reagent composition comprising fibrinogen

| | % plasminogen | | | | | | |
|---|---|---|---|---|---|---|---|
| Time | 150 1/20 | 75 1/40 | 37.5 1/80 | 18.75 1/160 | 0 0 | r2 (lin/lin) | ÄOD (150/0) |
| T0 (21/04/11) | 1.828 | 0.895 | 0.425 | 0.192 | 0.008 | 0.999 | 1.820 |
| T0 + 1 weeks (FB) | 1.479 | 0.681 | 0.306 | 0.128 | 0.000 | 0.997 | 1.479 |
| T0 + 2 weeks | 1.513 | 0.684 | 0.296 | 0.121 | 0.000 | 0.996 | 1.513 |
| T0 + 3 weeks | 1.387 | 0.637 | 0.274 | ** | ** | ** | ** |

** lack of substrate

These data demonstrate that there is substantial variability of OD determination using R1 maintained at 30° C. Without going beyond the scope of the invention, a person skilled in the art may adapt the method of the invention to an assay based on urokinase instead of streptokinase, with a corresponding activator, preferably a urokinase activator chosen from fibrin fragments.

The invention claimed is:

1. A method for assaying plasminogen in a sample comprising steps consisting of:
    a) storing a composition comprising a streptokinase and a streptokinase activator in a ready-to-use solution;
    b) reacting the composition with a control solution or a diluted plasma sample;
    c) tracking said reaction;
    d) determining the amount of plasminogen in the control solution or in the diluted plasma sample, as a function of the result of the tracking of said reaction, wherein the streptokinase activator is a fibrin DD fragment, at least one DD fragment derivative, or both a fibrin DD fragment and at least one DD fragment derivative.

2. The method according to claim 1, wherein the reaction step b) is performed in the presence of an anticoagulant.

3. The method according to claim 1, wherein the storage step is performed at a temperature of between −20° C. and 37° C.

4. The method according to claim 1, wherein the storage step is performed for a period greater than 12 hours.

5. The method according to claim 1, further comprising before the reaction step b), a step of pre-incubating the composition comprising the streptokinase and the streptokinase activator, at around 37° C.

6. The method according to claim 1, wherein the reaction step b) is performed at around 37° C.

7. The method according to claim 1, wherein the reaction step b) is stopped by an acidification step.

8. A method for assaying plasminogen in a sample comprising:
    storing a composition comprising streptokinase and a streptokinase activator in a ready-to-use solution;
    reacting the composition with a control solution or a diluted plasma sample;
    tracking the reaction of the streptokinase and the streptokinase activator with the control solution of the diluted plasma sample; and
    determining an amount of plasminogen in the control solution or in the diluted plasma sample based on the result of the tracking of the reaction,
    wherein the streptokinase activator is at least one selected from the group consisting of a fibrin DD fragment and at least one DD fragment derivative.

9. The method according to claim 8, wherein the tracking step is performed by using a chromogenic substrate specific for plasmin and plasmin-streptokinase complexes.

10. The method according to claim 8, wherein the reaction step is performed in the presence of an anticoagulant.

11. The method according to claim 8, wherein the storage step is performed at a temperature of between −20° C. and 37° C.

12. The method according to claim 8, wherein the storage step is performed for a period greater than 12 hours.

* * * * *